(12) United States Patent
Shelso

(10) Patent No.: US 7,208,002 B2
(45) Date of Patent: Apr. 24, 2007

(54) EXPANSION-ASSISTING DELIVERY SYSTEM FOR SELF-EXPANDING STENT

(75) Inventor: Susan I. Shelso, Plymouth, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 71 days.

(21) Appl. No.: 09/753,448

(22) Filed: Jan. 4, 2001

(65) Prior Publication Data

US 2002/0087186 A1 Jul. 4, 2002

(51) Int. Cl.
*A61F 2/06* (2006.01)
(52) U.S. Cl. .................................. 606/198; 623/1.11
(58) Field of Classification Search ................ 604/964; 606/108, 191, 192, 194, 198; 623/1.11, 1.34
See application file for complete search history.

(56) References Cited

U.S. PATENT DOCUMENTS

| 5,534,007 | A | * | 7/1996 | St. Germain et al. ...... 623/1.11 |
| 5,695,499 | A | * | 12/1997 | Helgerson et al. .......... 606/108 |
| 5,702,418 | A | * | 12/1997 | Ravenscroft ............... 623/1.11 |
| 5,709,703 | A | * | 1/1998 | Lukic et al. ................ 623/1.12 |
| 5,743,874 | A | * | 4/1998 | Fischell et al. ......... 604/103.04 |
| 5,749,921 | A | * | 5/1998 | Lenker et al. .............. 623/1.42 |
| 5,902,334 | A | * | 5/1999 | Dwyer et al. ............... 606/194 |
| 5,954,693 | A | | 9/1999 | Barry .......................... 604/96 |
| 6,056,759 | A | * | 5/2000 | Fiedler ....................... 606/191 |
| 6,221,081 | B1 | * | 4/2001 | Mikus et al. ............... 606/108 |

FOREIGN PATENT DOCUMENTS

| EP | 0699451 A2 | 3/1996 |
| EP | 0839504 A1 | 5/1998 |

* cited by examiner

*Primary Examiner*—Corrine McDermott
*Assistant Examiner*—Christopher Prone
(74) *Attorney, Agent, or Firm*—Hoffmann & Baron, LLP

(57) ABSTRACT

A delivery system for a self-expanding stent includes a catheter having a distal end and being configured to retain a self-expanding stent proximate the distal end. The delivery system also includes an inflatable device provided on the catheter and positioned proximate the distal end. The inflatable device, typically a balloon, is configured to selectively assist the self-expanding stent with radially expansion. The catheter includes a tubular member and an outer member coaxially positioned about the tubular member. The outer member can slide relative to the tubular member in an axial direction. The outer member is configured to retain a self-expanding stent in a radially-compressed position and to release the self-expanding stent to a radially-expanded position. The delivery system may also include a holding sleeve provided on the tubular member, spaced from the distal end of the catheter, and configured to hold the self-expanding stent. The delivery system preferably includes a loading funnel configured to be removably attachable to the distal end of the tubular member and configured to assist with radial compression of the self-expanding stent and advancement of the self-expanding stent within the outer member.

47 Claims, 1 Drawing Sheet

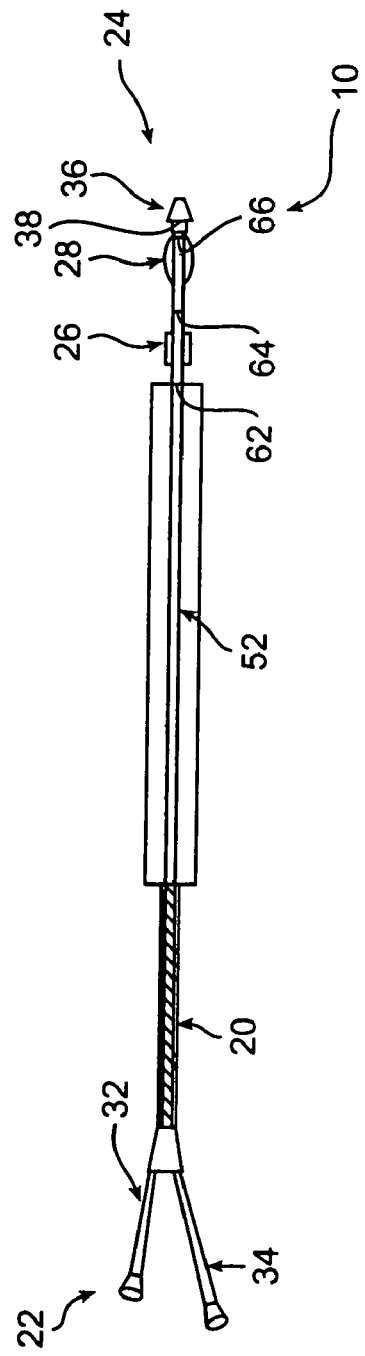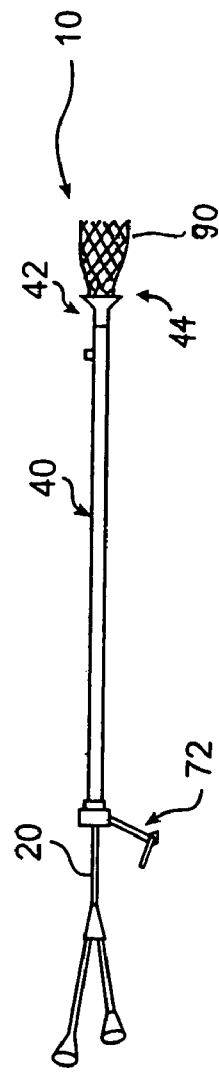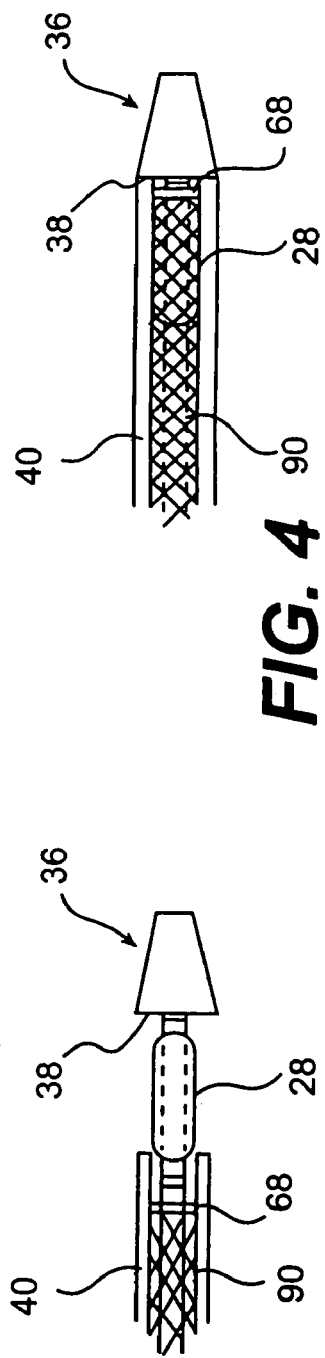

EXPANSION-ASSISTING DELIVERY SYSTEM FOR SELF-EXPANDING STENT

BACKGROUND OF THE INVENTION

1. Field of the Invention

The present invention relates to a system for delivery of a stent into the body of a patient. More particularly, the present invention relates to an expansion-assisting delivery system for a self-expanding stent.

2. Description of Related Art

Stents are well-known endoprostheses. A conventional endoprosthetic stent includes a radially-expandable, tubular structure. The tubular structure can expand radially from a compact form for delivery to an expanded form for implantation. Radial expansion of the stent effects implantation into the tissues of a vessel wall being repaired or bridged. The vessel can include, for example, a body canal, blood vessel, duct, other passage, and the like.

A conventional endoprosthetic stent can be mechanically expansive or self-expansive. A conventional mechanically-expansive stent initially possesses a radially compact form. The stent is loaded onto a delivery system, such as a catheter. Typically, an expandable balloon is positioned in the tubular structure of the stent. After delivering the stent to the region of a vessel being repaired or bridged, the balloon is expanded, thereby implanting the stent onto the vessel wall. To expand the stent, the balloon must be connected to a fluid source by means of a lumen or some other tubular structure.

A conventional self-expansive stent initially possesses a radially-expanded form. The stent is compressed radially as it is assembled onto a delivery system. Typically, an outer tubular structure retains the compressed stent until it is delivered to the region of a vessel being repaired or bridged. The stent is then released from its compressed state and self-expands to implant onto the vessel wall. An expandable balloon is not required to expand the stent. However, in cases where a stricture of the vessel is difficult to repair or bridge, a physician may use a balloon to assist with expansion of the deployed stent.

Generally, when a balloon is used to assist with expansion of a self-expanding stent, the conventional stent delivery system is removed after the stent is successfully deployed. Then, either a separate single-use balloon catheter or a second delivery system having an expandable balloon is delivered to the sight of the stent. In either event, a physician would be slowed by this process of removing the stent delivery system and delivering the balloon.

Conventional stent delivery systems generally include a minimal transverse dimension so is that a distal end of the delivery system can be navigated through and along a patient's lumens, or vessels, either in a percantaneous insertion procedure or through the working channel of an endoscope or laparoscope. Often times, physicians use a delivery system in combination with a medical guidewire. Typically, in transluminal procedures, the physician directs a guidewire through narrow passages, or vessels, in a patient's body using a steering mechanism provided at a proximal end outside of the body. The physician monitors the travel and position of a distal end of the guidewire by a fluoroscope or other known device. Once the distal end of the guidewire reaches a desired position, the steering mechanism is removed and the delivery system is directed into the vessel along the guidewire. Other procedures for directing catheters or similar devices into larger vessels of the body, such as the esophagus, are also well known.

Thus, use of a conventional delivery system for a self-expanding stent in combination with a guidewire and a post-deployment expandable balloon would require the following time-consuming procedures: delivery of the guidewire; delivery and deployment of the stent; removal of the stent delivery system; delivery and activation of an expandable balloon device; and removal of the balloon delivery system and guidewire. The repeated insertion and removal of delivery systems prolongs the procedure and thereby increases the trauma and risk to the patient and increases costs.

SUMMARY OF THE INVENTION

To overcome the disadvantages of the prior art, and in accordance with the purposes of the invention, as embodied and broadly described herein, there is provided an expansion-assisting delivery system for a self-expanding stent. The delivery system includes a catheter having a distal end and being configured to retain a self-expanding stent proximate the distal end. The delivery system also includes an inflatable device provided on the catheter and positioned proximate the distal end. The inflatable device is configured to selectively assist the self-expanding stent with radial expansion. In a preferred embodiment of the delivery system, the inflatable device is a balloon.

In accordance with the present invention, the catheter includes a tubular member and an outer member coaxially positioned about the tubular member. The outer member can slide relative to the tubular member in an axial direction. The outer member is configured to retain a self-expanding stent in a radially-compressed position and to release the self-expanding stent to a radially-expanded position. The delivery system may also include a holding sleeve provided on the tubular member and spaced from the distal end of the catheter. The holding sleeve can be configured to hold the self-expanding stent.

In a preferred embodiment the delivery system also includes a loading funnel configured to be removably attachable to the distal end of the tubular member. The loading funnel may be configured to assist with radial compression of the self-expanding stent and advancement of the self-expanding stent within the outer member.

Another preferred embodiment of the delivery system includes a spacing jacket coaxially positioned about the tubular member and inside the outer member. In yet another preferred embodiment, the delivery system includes a fluid port configured to receive a fluid and direct the fluid to a region between the tubular inner member and outer member.

In another preferred embodiment, the tubular inner member of the delivery system includes a first marker band indicating a position corresponding to a proximal end of a self-expanding stent, a second marker band indicating a position corresponding to a re-constrain limit of a partially-expanded, self-expanding stent, and a third marker band indicating a position corresponding to a distal end of a self-expanding stent. The third marker band is positioned nearest the distal end of the tubular inner member, and the second marker band is positioned between the first marker band and the third marker band. The tubular inner member may define first and second lumens, one receiving a guidewire, and the other providing a fluid passage to the inflatable device.

Another aspect of the invention provides a self-expanding stent in combination with a preferred embodiment of the delivery system of the invention.

In yet another aspect, the invention provides a method for implantation of a self-expanding stent including providing a preferred embodiment of the delivery system of the invention, delivering the delivery system to a region of a vessel to be repaired, implanting the self-expanding stent into a wall of the vessel to be repaired, and inflating the inflatable device to assist expansion of the self-expanding stent.

BRIEF DESCRIPTION OF THE DRAWINGS

The accompanying drawings, which are incorporated in and constitute part of the specification, illustrate a presently preferred embodiment of the invention and, together with the general description given above and detailed description of the preferred embodiments given below, serve to explain the principles of the invention.

FIG. 1 is a plan view of a preferred embodiment of a partially-assembled delivery system according to the invention;

FIG. 2 is a plan view of a preferred embodiment of an assembled delivery system according to the invention;

FIG. 3 is a partial, sectional view of the delivery system illustrated in FIG. 2; and FIG. 4 is an alternative partial, sectional view of the delivery system illustrated in FIG. 2.

DESCRIPTION OF THE PREFERRED EMBODIMENTS

Reference now will be made in detail to the present preferred embodiments of the invention, examples of which are illustrated in the accompanying drawings, in which like numerals designate like elements.

In accordance with the present invention, there is provided a delivery system for a self-expanding stent. As embodied herein and shown in FIGS. 1–3, the present invention includes a catheter 10 adapted to deploy a self-expanding stent. The stent may, for example, repair or bridge a damaged vessel of a patient's body. The catheter 10 includes an inner member 20 and an outer member 40. Preferably, the inner and outer members 20, 40 are tubular-shaped. In a preferred embodiment, a portion of inner member 20 may be formed of stainless steel. However, the invention in its broadest sense is not limited by the shape, size, composition, or type of the inner member 20.

FIG. 1 illustrates the delivery system with the outer member 40 removed. In FIG. 1, the inner member 20 has a proximal end 22 and a distal end 24. Spaced from the distal end 24, the inner member 20 includes a holding sleeve 26. The holding sleeve 26 is preferably coaxially mounted about the inner member 20 and is sized and configured such that a self-expanding stent 90 can be placed around it. The holding sleeve 26 can retain the positioning of the stent 90 during delivery and re-constrain procedures by cooperating with the outer member 40 to prevent axial movement of the stent.

The inner member 20 is also provided with an inflatable device 28 positioned between the holding sleeve 26 and the distal end 24. Preferably, the inflatable device 28 is coaxially mounted about the inner member 20 and, when deflated, has a small enough radial component that a coaxially-mounted, self-expanding stent can pass over the inflatable device 28. The inflatable device 28 is preferably a balloon, such as a biliary balloon or the like known in the art. The inflatable device 28 may also function as a holding sleeve 26 in some configurations, negating the need for a separate holding sleeve device 26.

As shown in FIG. 1, the inner member 20 preferably includes a first lumen tube 32 and a second lumen tube 34. The first lumen tube 32 is configured to receive a medical guidewire (not shown), and the second lumen tube 34 provides a fluid passage to the inflatable device 28. The configuration of the lumen tubes can be reversed such that the first lumen tube provides a fluid passage to the inflatable device 28 and the second lumen tube receives a medical guidewire.

In a preferred embodiment of the invention, the distal end 24 of the inner member 20 includes a tapered tip 36. The tapered tip 36 may provide easier delivery and maneuverability, particularly when using the delivery system in combination with a medical guidewire. In addition, the tapered tip 36 includes a surface 38 extending radially outward from the inner member 20 and forming a seat against which the outer member 40 can rest.

FIG. 2 illustrates the delivery system with the outer member 40 coaxially positioned about the inner member 20. The outer member is slidably mounted about the inner member to permit relative axial movement between them. As shown in FIG. 2, the catheter 10 may also include a loading funnel 42 removably attached to a distal end 44 of the outer member. The loading funnel 42 is sized and shaped to assist with radial compression of a self-expanding stent 90 as the stent 90 is loaded onto the delivery system, as shown in FIG. 2.

FIG. 3 illustrates the delivery system in combination with a self-expanding stent 90. The stent 90 may be made of bioabsorbable poly-l-lactide filaments braided in a tubular mesh configuration. However, the invention in its broadest sense is not limited by the shape, size, composition. or type of the self-expanding stent 90.

A self-expanding stent 90 may be operatively loaded onto the delivery system at the distal end of the catheter 10 passing over the inflatable device 28 and holding sleeve 26. As shown in FIG. 3, the self-expanding stent 90 is retained in a radially-compressed position by the outer member 40, and the inflatable device 28 is provided on the catheter 10 between the self-expanding stent 90 and the distal end of the catheter 10. As shown in FIG. 4, the inflatable device 28 may alternatively be positioned beneath the distal portion of the self-expanding stent 90. The outer member 40 releases the self-expanding stent 90 to a radially-expanded position as the outer member 40 slides relative to the inner member 20 in a direction away from the seat 38.

In a preferred embodiment, the delivery system includes a spacing jacket 52 coaxially positioned about the inner member 20 and inside the outer member 40. The spacing jacket 52 may reduce snaking, coiling, or twisting of the inner member within the outer member, particularly during delivery through a tortuous anatomy.

According to another preferred embodiment of the delivery system, the inner member 20 includes first, second, and third marker bands 62, 64, 66. As shown in FIG. 1, the third marker band 66 is positioned nearest the distal end 24 of the inner member 20 and the second marker band 64 is positioned between the first marker band 62 and the third marker band 66.

In a preferred embodiment, a self-expanding stent extends from the first marker band 62 to the third marker band 66, in which case, the first marker band 62 indicates the position of a proximal end of the self-expanding stent 90, and the third marker band 66 indicates the position of a distal end of the self-expanding stent 90. The second marker band 64 indicates a re-constrain limit of a partially-expanded, self-expanding stent.

The re-constrain limit signifies the final point to which a stent can be partially-expanded while still providing a physician or other operator with the ability to successfully re-constrain, re-position, and re-expand the stent. That is, once a self-expanding stent is loaded onto the delivery system, a physician can move the outer member 40 in an axial direction away from the distal end 24 of inner member 20 to allow expansion of the self-expanding stent. As long as the outer member 40 does not reach the second marker band 64, the physician may re-constrain the self-expanding stent by moving the outer member 40 in an axial direction toward the distal end 24 of inner member 20. However, once the distal end of the outer member 40 passes the second marker band 64. The possibility of stent deployment or slip with respect to the delivery system increases.

In an alternative embodiment, as shown in FIG. 3, the stent 90 may not extend to the seat 38 of the tapered end 36 of the inner member 20. In this case, a stent marker band 68 indicating the position of a distal end of the stent 90 may be provided on the stent 90 itself.

The marker bands 62, 64, 66, 68 are preferably formed of a material that would facilitate imaging during delivery of the delivery system and deployment of the stent. For example, the marker bands 62, 64, 66, 68 may be radiopaque marker bands or the like.

In a further preferred embodiment, the delivery system includes a fluid port 72. The fluid port 72 may be a conduit having a stopcock for connecting a syringe or any other device known in the art. The fluid can be used to flush the region between the inner member 20 and outer member 40.

According to another aspect, the invention includes a method for expansion-assisted implantation of a self-expanding stent. The method of the invention utilizes a catheter having coaxial inner and outer members according to an embodiment described above. Using sterile techniques, a self-expanding stent is loaded onto the catheter. To load the stent, a loading funnel is removably attached to a distal end of the outer member. The distal end of the outer member is slidably retracted away from the distal end of the inner member in the axial direction of the catheter. A physician causes relative movement between the inner member and the outer member with loading funnel by holding the inner member at, for example, the distal end or proximal end and slidably moving the outer member relative to the inner member in an axial direction away from the distal end of the inner member.

As the outer member is retracted, a holding sleeve mounted about the inner member is exposed. A physician or other user passes the stent over the tip of the distal end of the inner member and onto the holding sleeve. To do so, the user gently compresses the stent in a radially direction and fits it into the loading funnel until a proximal end of the stent reaches a proximal, or trailing, marker band. While holding the stent stationary in a radially-compressed configuration, the loading funnel is advanced back toward the distal end of the inner member. Again, the relative movement between the inner member and the outer member with loading funnel is effectuated by holding the inner member at, for example, the distal end or proximal end and slidably moving the outer member relative to the inner member in an axial direction toward the distal end of the inner member. The outer member is advanced until the stent is fully constrained between the inner member and outer member and between the holding sleeve and outer member.

The user delivers the delivery system along a medical guidewire or through an endoscope or laparoscope to the area of the vessel to be repaired or bridged. Once delivered to the appropriate location, the stent is released and allowed to self-expand, thereby implanting itself onto the vessel wall. Release is effectuated by sliding the outer member in a direction away from the distal end of the inner member. As discussed above, the stent can be successfully re-constrained, re-positioned, and re-expanded if desired, provided that the outer member is not moved beyond the re-constrain limit, or second marker band, in a direction away from the distal end of the inner member.

After the stent has been implanted, a physician or other user may determine that the stent is not sufficiently expanded. This determination may be accomplished with known imaging techniques such as, for example, the use of radiopaque markings on the stent. The delivery system of the above embodiments provides the user with the ability to selectively assist an incomplete or improper expansion by using the inflatable device provided on the catheter. Instead of requiring removal of the delivery system and delivery of an expansion balloon, the delivery system of the invention includes re-positioning of the already-deployed delivery system so that the inflatable device is properly aligned with the self-expanded stent. Since the inflatable device is positioned adjacent or beyond the distal end of the stent, re-positioning of the delivery system does not entail any further invasion into the patient's anatomy.

Typically, the inflatable device is properly positioned by slightly retracting the delivery system from the point of implantation of the stent. A fluid source, such as an air or saline source, supplies fluid to expand the inflatable device by way of the first or second lumen tube, depending on the system configuration. The inflatable device assists with complete and proper expansion of the stent. The inflatable device is then deflated prior to the delivery system being withdrawn from the patient's anatomy.

In accordance with an embodiment of the invention, the delivery system may include an inflatable device extending over the entire length of the self-expanding stent and coated with a tacky material. If the material was tacky enough to retain the stent during deploy and re-constrain procedures, the holding sleeve could be eliminated.

It should also be appreciated that a physician or other user may not need to use the inflatable device for every stent implantation. However, the delivery system of the invention makes the inflatable device available for selective usage by the physician. Therefore, the delivery system of the invention eliminates the need for an additional balloon delivery device and an additional step in the procedure. As a result, the delivery system reduces the implantation procedure time. Moreover, the delivery system of the invention ensures that the appropriate size inflatable device corresponding to the particular self-expanding stent is available for use, reducing the chance of over-dilating a vessel.

While this invention has been described with specific embodiments thereof, it is evident that many alternatives, modifications, and variations will be apparent to those skilled in the art. Accordingly, the preferred embodiments of the invention as set forth herein is intended to be illustrative, not limiting. Various changes may be made without departing from the spirit and scope of the invention.

I claim:

1. A delivery system for a self-expanding stent, the delivery system comprising:
   a catheter having a distal end, the catheter being configured to retain a self-expanding stent proximate the distal end, the catheter including
      a tubular member including a first marker band at a position corresponding to a distal most leading end of the self-expanding stent to indicate a position of the distal most leading end, a second marker band at a position corresponding to a trailing end of the self-expanding stent to indicate a position of the trailing end, and a third marker band between the first and second marker bands and between the leading and trailing ends of the stent, and an outer member positioned about the tubular member, the outer member being slidable relative to the tubular member in an axial direction;

a holding sleeve positioned about the tubular member and configured to retain the positioning of the stent, wherein the holding sleeve is positioned within an interior of the stent; and an inflatable device positioned about the tubular member, wherein there is no more than one inflatable device, wherein said inflatable device is disposed solely between the holding sleeve and the distal end of the catheter, and wherein at least a portion of the self-expanding stent overlaps a portion of the inflatable device prior to deployment of the self-expanding stent.

2. The delivery system of claim 1, wherein the outer member is configured to retain a self-expanding stent in a radially-compressed position and to release the self-expanding stent to a radially-expanded position.

3. The delivery system of claim 2, wherein the inflatable device is a balloon configured to selectively assist the self-expanding stent with radial expansion.

4. The delivery system of claim 1, further comprising a spacing jacket coaxially positioned about the tubular member and inside the outer member.

5. The delivery system of claim 1, further comprising a fluid port, the fluid port configured to receive a fluid and direct the fluid to a region between the tubular member and outer member.

6. The delivery system of claim 1, wherein the distal end of the tubular member includes a tapered tip.

7. The delivery system of claim 6, wherein the tapered tip includes a surface extending radially outward from the tubular member to form a seat to receive the outer member.

8. The delivery system of claim 1, wherein the third marker band indicates a position corresponding to a re-constrain limit of a partially-expanded, self-expanding stent.

9. The delivery system of claim 1, wherein the tubular member defines a first lumen and a second lumen, one of the first lumen and the second lumen configured to receive a guidewire, and the other of the first lumen and the second lumen providing a fluid passage to the inflatable device.

10. The delivery system of claim 1, wherein at least one of the first, second, and third marker bands is a radiopaque marker band.

11. The delivery system of claim 1, wherein the inflatable device is a balloon.

12. In combination, a self-expanding stent and a delivery system for the self-expanding stent, the combination comprising:
the delivery system of claim 1; and
a self-expanding stent mounted on the delivery system.

13. The delivery system of claim 1, wherein the holding sleeve is spaced apart from the inflatable device.

14. A delivery system for a self-expanding stent, the delivery system comprising:
a catheter having a distal end, the catheter being configured to retain a self-expanding stent proximate the distal end, the catheter including
a tubular member including a first marker band at a position corresponding to a distal most leading end of the self-expanding stent, a second marker band at a position corresponding to a trailing end of the self-expanding stent, and a third marker band between the first and second marker bands, and an outer member positioned about the tubular member, the outer member being slidable relative to the tubular member in an axial direction;

a holding sleeve positioned about the tubular member and configured to retain the stent, wherein the holding sleeve is positioned within an interior of the stent;

an inflatable device positioned about the tubular member, wherein there is no more than one inflatable device, wherein said inflatable device disposed solely between the holding sleeve and the distal end of the catheter; and a loading funnel, the loading funnel being configured to be removably attachable to a distal end of the tubular member and to receive the stent therein as the stent is loaded onto the delivery system.

15. The delivery system of claim 14, wherein the loading funnel is configured to assist with radial compression of the self-expanding stent and advancement of the self-expanding stent within the outer member.

16. The delivery system of claim 14, wherein the holding sleeve is spaced apart from the inflatable device.

17. A method for implantation of a self-expanding stent, the method comprising:
attaching a funnel to a distal end of a delivery system, the delivery system including a catheter having a distal end and being configured to retain a self-expanding stent proximate the distal end, the catheter including a first marker band at a position corresponding to a distal most leading end of the self-expanding stent, a second marker band at a position corresponding to a trailing end of the self-expanding stent, and a third marker band between the first and second marker bands, a holding sleeve configured to retain the stent, and an inflatable device provided on the catheter and positioned beneath at least a portion of the self-expanding stent prior to deployment of the self-expanding stent, wherein there is no more than one inflatable device, wherein the inflatable device is disposed solely between the holding sleeve and the distal end of the catheter, and wherein the holding sleeve is positioned within an interior of the stent;
loading a self-expanding stent onto the delivery system through the funnel;
delivering the delivery system to a region of a vessel to be repaired;
implanting the self-expanding stent into a wall of the vessel to be repaired; and
inflating the inflatable device to assist expansion of the self-expanding stent.

18. The method of claim 17, wherein delivering the delivery system includes:
positioning a medical guidewire; and
guiding the delivery system with the guidewire to the area of the vessel to be repaired.

19. The method of claim 17, wherein delivering the delivery system includes:
positioning an endoscope; and
guiding the delivery system through an endoscope to the area of the vessel to be repaired.

20. The method of claim 17, wherein providing a delivery system includes providing the catheter with a tubular member and an outer member coaxially positioned about the tubular member, the outer member being slidable relative to the tubular member in an axial direction.

21. The method of claim 20, wherein implanting the self-expanding stent includes effectuating relative axial movement between the tubular member and outer member to release the stent and allow the stent to self-expand.

22. The method of claim 17, wherein inflating the inflatable device includes re-positioning the already-delivered delivery system such that the inflatable device is properly aligned with the self-expanded stent.

23. The method of claim 22, wherein re-positioning the already-delivered delivery system includes slightly retracting the delivery system from the point of implantation of the stent.

24. The method of claim 17, wherein inflating the inflatable device includes supplying fluid to the inflatable device.

25. The method of claim 24, wherein supplying fluid includes supplying air.

26. The method of claim 24, wherein supplying fluid includes supplying fluid by way of a lumen tube extending through the catheter.

27. The method of claim 17, further comprising:
deflating the inflatable device; and
withdrawing the delivery system from a patient's anatomy.

28. The method of claim 17, wherein the holding sleeve is spaced from the inflatable device.

29. In combination, a self-expanding stent and a delivery system for the self-expanding stent, the combination comprising:
a self-expanding stent;
a catheter having a distal end, the catheter being configured to retain the self-expanding stent proximate the distal end, the catheter including a tubular member having a first marker band at a position corresponding to a distal most leading end of the self-expanding stent to indicate a position of the distal most leading end, a second marker band at a position corresponding to a trailing end of the self-expanding stent to indicate a position of the trailing end, and a third marker band between the first and second marker bands and between the leading and trailing ends of the stent;
a holding sleeve positioned about the tubular member and configured to retain the stent, wherein the holding sleeve is positioned within an interior of the stent; and
an inflatable device positioned about the tubular member, wherein there is no more than one inflatable device, at least a portion of the self-expanding stent overlapping at least a portion of the inflatable device prior to deployment of the self-expanding stent, wherein the inflatable device is disposed solely between the holding sleeve and the distal end of the catheter.

30. The combination of claim 29, wherein the catheter includes an outer member coaxially positioned about the tubular member, the outer member being slidable relative to the tubular member in an axial direction.

31. The combination of claim 30, wherein the outer member is configured to retain the self-expanding stent in a radially-compressed position and to release the self-expanding stent to a radially-expanded position.

32. The combination of claim 30, further comprising a spacing jacket coaxially positioned about the tubular member and inside the outer member.

33. The combination of claim 30, wherein the third marker band indicates a position corresponding to a re-constrain limit of the self-expanding stent when in a partially-expanded state.

34. The combination of claim 30, wherein the tubular member defines a first lumen and a second lumen, one of the first lumen and the second lumen configured to receive a guidewire, and the other of the first lumen and the second lumen providing a fluid passage to the inflatable device.

35. The combination of claim 29, wherein the holding sleeve is spaced from the inflatable device.

36. In combination, a self-expanding stent and a delivery system for the self-expanding stent, the combination comprising:
a self-expanding stent;
a catheter having a distal end, the catheter being configured to retain the self-expanding stent proximate the distal end, the catheter including
a tubular member including a first marker band at a position corresponding to a distal most leading end of the self-expanding stent, a second marker band at a position corresponding to a trailing end of the self-expanding stent, and a third marker band between the first and second marker bands, and
an outer member coaxially positioned about the tubular member, the outer member being slidable relative to the tubular member in an axial direction;
a holding sleeve positioned about the tubular member and configured to retain the stent, wherein the holding sleeve is positioned within an interior of the stent;
an inflatable device provided on the catheter, wherein there is no more than one inflatable device, at least a portion of the self-expanding stent overlapping at least a portion of the inflatable device, wherein the inflatable device is disposed solely between the holding sleeve and the distal end of the catheter; and
a loading funnel, the loading funnel being configured to be removably attachable to a distal end of the tubular member and to receive the stent therein as the stent is loaded onto the delivery system.

37. The combination of claim 36, wherein the holding sleeve is spaced from the inflatable device.

38. A delivery system for a self-expanding stent, the delivery system comprising:
a catheter having a distal end, the catheter being configured to retain a self-expanding stent proximate the distal end, the catheter including a first marker band at a position corresponding to a distal most leading end of the self-expanding stent, a second marker band at a position corresponding to a trailing end of the self-expanding stent, and a third marker band between the first and second marker bands;
a holding sleeve positioned about the tubular member and configured to retain the stent, wherein the holding sleeve is positioned within an interior of the stent;
an inflatable device provided on the catheter and positioned proximate the distal end, wherein there is no more than one inflatable device, wherein the inflatable device is disposed solely between the holding sleeve and the distal end of the catheter; and
a loading funnel configured to be removably attachable to the distal end of the catheter and to receive the stent therein as the stent is loaded onto the delivery system.

39. The delivery system of claim 38, wherein the catheter includes a tubular member and an outer member positioned about the tubular member, the outer member being slidable relative to the tubular member in an axial direction.

40. The delivery system of claim 39, wherein the loading funnel is configured to assist with radial compression of the self-expanding stent and advancement of the self-expanding stent within the outer member.

41. The delivery system of claim 39, further comprising a spacing jacket coaxially positioned about the tubular member and inside the outer member.

42. The delivery system of claim 39, wherein the tubular member includes the first marker band, the second marker band, and the third marker band, wherein the third marker band indicates a position corresponding to a re-constrain limit of a partially-expanded, self-expanding stent.

43. The delivery system of claim 39, wherein the tubular member defines a first lumen and a second lumen, one of the first lumen and the second lumen configured to receive a guidewire, and the other of the first lumen and the second lumen providing a fluid passage to the inflatable device.

44. In combination, a self-expanding stent and a delivery system for the self-expanding stent, the combination comprising:

the delivery system of claim 38; and a self-expanding stent mounted on the delivery system.

45. The delivery system of claim 38, wherein the holding sleeve is spaced from the inflatable device.

46. A method for implantation of a self-expanding stent, the method comprising:

providing a delivery system including a self-expanding stent, a catheter having a distal end and being configured to retain the self-expanding stent proximate the distal end and including a tubular member having a first marker band at a position corresponding to a distal most leading end of the self-expanding stent to indicate a position of the distal most leading end, a second marker band at a position corresponding to a trailing end of the self-expanding stent to indicate a position of the trailing end, and a third marker band between the first and second marker bands and between the leading and trailing ends of the stent, a holding sleeve positioned about the tubular member and configured to retain the stent, and an inflatable device provided on the catheter and positioned beneath at least a portion of the self-expanding stent prior to deployment of the self-expanding stent, wherein there is no more than one inflatable device, wherein the inflatable device is disposed solely between the holding sleeve and the distal end of the catheter, and wherein the holding sleeve is positioned within an interior of the stent;

delivering the delivery system to a region of a vessel to be repaired;

releasing a portion of the self-expanding stent to a position corresponding with the third marker band on the catheter;

re-constraining the self-expanding stent;

implanting the self-expanding stent into a wall of the vessel to be repaired; and inflating the inflatable device to assist expansion of the self-expanding stent.

47. The method of claim 46, wherein the holding sleeve is spaced from the inflatable device.

* * * * *